US011298448B2

(12) United States Patent
Scagliarini et al.

(10) Patent No.: US 11,298,448 B2
(45) Date of Patent: Apr. 12, 2022

(54) FILTER UNIT FOR WHOLE BLOOD AND BLOOD DERIVATIVES

(71) Applicant: GVS S.P.A., Zola Predosa (IT)

(72) Inventors: Massimo Scagliarini, Casalecchio di Reno (IT); Luca Querze', San Lazzaro di Savena (IT); Filippo Trascinelli, Sala Baganza (IT)

(73) Assignee: GVS S.P.A., Zola Predosa (IT)

( * ) Notice: Subject to any disclaimer, the term of this patent is extended or adjusted under 35 U.S.C. 154(b) by 0 days.

(21) Appl. No.: 16/772,446

(22) PCT Filed: Dec. 11, 2018

(86) PCT No.: PCT/IB2018/059867
§ 371 (c)(1),
(2) Date: Jun. 12, 2020

(87) PCT Pub. No.: WO2019/116220
PCT Pub. Date: Jun. 20, 2019

(65) Prior Publication Data
US 2021/0085852 A1      Mar. 25, 2021

(30) Foreign Application Priority Data

Dec. 13, 2017   (IT) .......................... 102017000143635

(51) Int. Cl.
*A61M 1/36*      (2006.01)

(52) U.S. Cl.
CPC .................................. *A61M 1/3635* (2014.02)

(58) Field of Classification Search
CPC .............. A61M 1/3635; A61M 1/3636; A61M 1/3633; A61M 1/0218; A61M 1/0272;
(Continued)

(56) References Cited

U.S. PATENT DOCUMENTS 5,543,062 A * 8/1996 Nishimura .......... A61M 1/0209
                                                             210/257.1
5,688,460 A     11/1997 Ruschke
                 (Continued)

FOREIGN PATENT DOCUMENTS

| EP | 3053610 A1 | 8/2016 |
| EP | 3053612 A1 | 8/2016 |
| WO | 2001091880 | 12/2001 |

OTHER PUBLICATIONS

International Search Report dated Feb. 11, 2019.

*Primary Examiner* — Krishnan S Menon
(74) *Attorney, Agent, or Firm* — Dickinson Wright PLLC

(57) ABSTRACT

A filter unit for blood and blood derivatives comprises a body defined by two injection-moulded half-shells of thermoplastic polymer material, there being present between said half-shells a cavity containing a filtering element having two opposing flat faces, an inlet opening and an outlet opening made on the opposing outer surfaces of said body communicating with said cavity. Each of said half-shells comprises a projecting perimetral flange, the flanges of the overlapping half-shells being welded together to form a flange of the body of the filter unit and connect the two half-shells together, the filtering element being wholly contained within the cavity of such body and pressed by shelves projecting into such cavity from each half-shell in the vicinity of its perimetral border and on the two opposing faces, said shelves retaining said filtering element in a stable position within cavity, said thermoplastic polymer material being yielding and semi-rigid.

10 Claims, 5 Drawing Sheets

(58) Field of Classification Search
CPC .............. A61M 1/3693; A61M 1/3616; A61M 2205/0216; A61M 2202/0439; B01D 35/30
See application file for complete search history.

(56) References Cited

U.S. PATENT DOCUMENTS

| | | | |
|---|---|---|---|
| 5,707,520 A * | 1/1998 | Kuroki | A61M 1/3633 210/188 |
| 7,807,026 B2 | 10/2010 | Tettamanti et al. | |
| 2001/0037978 A1 | 11/2001 | Calhoun et al. | |
| 2007/0199897 A1 | 8/2007 | Ozeki et al. | |
| 2010/0108596 A1 | 5/2010 | Duhaut et al. | |
| 2018/0154053 A1* | 6/2018 | Shimada | A61M 1/34 |

* cited by examiner

FILTER UNIT FOR WHOLE BLOOD AND BLOOD DERIVATIVES

RELATED APPLICATIONS

This application claims priority to Italian Patent Application No. 102017000143635, filed Dec. 13, 2017, and PCT/IB2018/059867, filed Dec. 11, 2018, the entire contents of which are incorporated herein by reference in their entirety.

FIELD

The object of the present disclosure is a filter unit for whole blood and blood derivatives according to the precharacterising clause of the principal claim.

BACKGROUND

The use of filter units in both laboratories and hospitals in order to separate out a patient's blood into its components is known. Each filter unit in particular comprises a body of flexible polymer material, said body normally being obtained through joining together two shells bounding an internal cavity of the body in which a filter means or element is located, for example one suitable for filtering out the leucocytes present in blood. The body comprises an inlet opening and an outlet opening to allow the blood to be filtered to enter and leave the filter unit. The shells are joined together along their perimetral edges.

During the separation of blood derivatives each unit is then centrifuged, forming a part together with a bag of whole blood and various bags for collecting the blood derivatives in a sterile set forming a closed circuit.

Filters made of rigid material (PVC, acrylics, or others) which are centrifuged, sometimes at high speed, may become cracked or broken due to impacts generated within the rotor of the centrifuge.

In addition to this, impact against other components of the set can cause these to burst, with obvious consequences for the possible subsequent use of the centrifuge because of the loss of blood content (contamination of both).

US2001/0037978 describes a filter for filtering fluids such as whole blood and blood derivatives comprising a first and second containment shell formed of flexible thermoplastic polymer material such as PVC through moulding processes. Through the use of such material the filter unit or filter can collapse and expand according to the presence of a non-compressible fluid (for example a fluid such as blood) or a combination of fluids (such as air and blood) within it; when the volume of liquid falls, the filter unit collapses on itself, reducing its internal volume, avoiding the occurrence of foaming. This makes it possible to overcome the disadvantage which occurs with a rigid and non-flexible filter unit, where the simultaneous passage of air and liquid gives rise to said foaming.

US2001/0037978 cites a state of the art in which filters are obtained through using rigid plastics, for example acrylics, of polypropylene.

The prior document also describes a state of the art comprising filters constructed from one or more flexible PVC sheets which nevertheless have the disadvantage that it is difficult to construct openings for a leaktight connection between the filter and the normal tubes for entry and departure of the fluid (for example, blood) to be filtered, to and from such filter.

US2001/0037978 describes a filter with openings made of one piece with the shells of the filter itself. In addition to this, this filter provides that an internal filter element or membrane ends at the perimetral edges of the shells and is held in a stable position within the body of the filter by the means through which the edges of the two shells are attached (normally by welding through local heating or ultrasound). However this solution has the disadvantage that the filter or filter element can deform close to the edges within the cavity of the filter unit, which compromises optimum use of its filtering action.

US2006/0049097 relates to a filter, in particular for separating leucocytes from other blood components, comprising an outer enclosure or casing and having at least one intermediate layer which is part of the frame or forms a frame, having an inlet chamber which is in communication with an inlet for the medium which has to be filtered and an outlet chamber which communicates with an outlet for the filtrate. These chambers are separated by a filter material.

The outer casing or enclosure is made of flexible material such as PVC. The outer casing is welded to the intermediate layer.

The filter material is pressed together and welded to the outer casing or enclosure and to the intermediate layer. This is brought about through a first weld within the filter, and a second weld connecting the two shells defining the outer enclosure, at the free edge of the latter.

Filter material is present between the two welds so as not to create empty spaces at the inlet to the filter means within the filter.

WO01/91880 describes a system for collecting blood comprising a blood container and a filter communicating with the container arranged so as to aid handling as a single piece. The filter comprises two flexible shells of medical grade plastics material which contain a filter medium.

The shells are connected together by means of two consecutive concentric welds and as a result of this a soft cushion is created at the periphery of the filter around filter 20 which gives rise to improved protection against possible damage during handling of the filter between the abovementioned system and the tubes and other containers used in such system when the latter is moved as a whole, for example during the normal centrifuging operations to which it is subjected.

US2010/0108596 also relates to a filter unit or filter capable of selectively eliminating particular substances (such as leucocytes, pathogens, proteins) from a fluid such as blood or blood derivatives. The unit or filter is flexible and comprises two flexible sheets welded together at their peripheral edges between which a filter material is located.

US2007/0199897 describes a method for filtering blood and blood components and a filter device having a container which is preferably obtained from sheet materials of flexible synthetic resin such as PVC, polyurethane or other thermoplastic elastomers. This filter device comprises a filter material to remove substances from blood, such as leucocytes, with particular thicknesses and filter areas, generating a particular pressure drop in the filter device. The filter material is placed in the container having a flat configuration provided with an inlet for blood (or a blood derivative) for filtration and an outlet for filtered blood. The container may have any shape (polygonal, curved) and matches that of the filter material. A body which contains and bounds the container on the outside is also provided.

EP3053610 describes a filter for processing blood comprising a flexible container on the inlet side and a flexible container on the outlet side, said containers closing off a filter element, an inlet opening and an outlet opening in the manner of a sandwich. The filter unit also comprises: a body providing a path for the fluid, a first sealed portion and a second sealed portion in which said body which provides a path for the fluid comprises a pair of opposing ribs. The outlet opening is located between said ribs. This body providing a path for the fluid comprises a slot made within the pair of ribs and diffusion openings located outside the pair of ribs which open continuously towards lateral portions of the first sealed portion.

This prior document starts from the state of the art defined by filtering units having a rigid container; however such a container is known to be able to damage the components of a centrifuge used to separate out blood constituents, and in particular leucocytes.

For this reason, EP3053610 describes the use of a flexible container to construct such a filter unit. This solution is however reported to have a tendency to give rise to swelling and/or flattening of the container during the process of separating blood into its components. For this reason, above all to prevent the container from collapsing onto the internal filter element, a device is provided to ensure flow within the container (flow path securing sheet).

EP3053612 relates to a filter unit for processing blood to remove undesirable components from blood or blood derivatives; the filter comprises: a filter element in sheet form, and a container comprising an element or component of a container on the inlet side and an element or part of a container on the outlet side arranged so as to hold the filter element tightly between them. Within the container the space is separated by the filter element into an inlet space and an outlet space. The filter element comprises a filter surface on the side of the inlet space, a filter surface on the side of the outlet space and an edge surface along the periphery of said filter surfaces. The element of the container on the inlet side and the element of the container on the outlet side are provided with a gripping member (gripper) which tightens and presses part of the outer edge of the pair of filter surfaces of the filter element. The gripper is made to adhere to the edge surface with a molten resin.

This prior document describes the use of container elements on the inlet side and outlet side which can be made of flexible resin so as to form a flexible container.

As an alternative, EP3053612 describes that the material of the container may be of rigid material.

However, EP3053612 does not describe that the container may be of semi-rigid and yielding material. The known solution therefore has the following disadvantages: if the container is of flexible material, it can swell or collapse onto the filter element when subjected to pressure changes when the blood within it is processed. If instead the container is of rigid material, this can damage the components of a centrifuge in which the container is placed to separate out whole blood into its blood components.

Furthermore the container does not comprise two parts welded together, but the container is obtained through moulding its parts in half-moulds which when closed make it possible to create the finished container. One of such parts is moulded onto the filter element. The gripper inserted in the closed mould to obtain the container with the inserted filter element makes it possible to join the parts of the container and the filter element together.

No welding of the parts of the container is provided for, but instead injection of the gripper as a necessary means for joining the said parts is provided.

Nothing is said concerning the packing factor of the filter unit.

U.S. Pat. No. 5,688,460 describes a process for producing hermetically sealed filter units and a product made therewith. The process comprises aligning a porous filter element between two parts of an enclosure and a thermoplastic edge (skirt) which overlaps the edge of at least one part of the enclosure to shield the edge of the filter element located adjacent to said edge or skirt, subjecting the two parts of the enclosure to pressure and then injection moulding an overmoulded strip of thermoplastic material around the outer portions of the parts of the enclosure to form a leaktight seal at the edge of the filter element.

BRIEF SUMMARY

This disclosure in the known art solves the problem of avoiding the phenomenon of jetting of the thermoplastic material into the filter unit during moulding.

No perimetral weld between the two parts of said unit is provided for.

The object of the present disclosure is to provide a filter unit for blood and blood derivatives which is improved in comparison with known units.

In particular, the object of the disclosure is to provide a filter unit in which the body is made so that it cannot break components within the centrifuge in which it is placed when whole blood is separated into its blood components.

Another object is to provide a filter unit having an internal filter element of high efficiency throughout its entire body.

A further object is to provide a filter unit which is soft to touch and easy to handle.

Another object is to provide a filter unit in which the filter element is held stably in position and flat within the cavity of said unit without it being subjected to heat-generating treatments used to join the shells of said unit as occurs in the solutions in the abovementioned state of the art where the filter element is welded to the body of the filter unit.

Another object is to provide a filter unit of the type mentioned in which the shells can be joined together effectively and for a long time.

A further object is to provide a filter unit which has high filtering efficiency.

These and other objects which will be apparent to those skilled in the art are accomplished through a filter unit according to the appended claims.

BRIEF DESCRIPTION OF THE DRAWINGS

For a better understanding of the present disclosure the following drawings are attached purely for indicative but non-limiting purposes, and in these.

DETAILED DESCRIPTION

With reference to the figures mentioned, a filter unit according to the disclosure comprises a body 1 defined by two half-shells 2 and 3 joined together and bounding a cavity or internal space 4 in which is placed a filter element 5 subdividing such cavity into two parts, a first cavity part 4A and a second cavity part 4B. Filter element 5 is defined, in a way in which it is in itself known, by a modular pack of filter layers which can be assembled according to the fluid to be filtered and/or the desired filtering effect.

Figure 1:
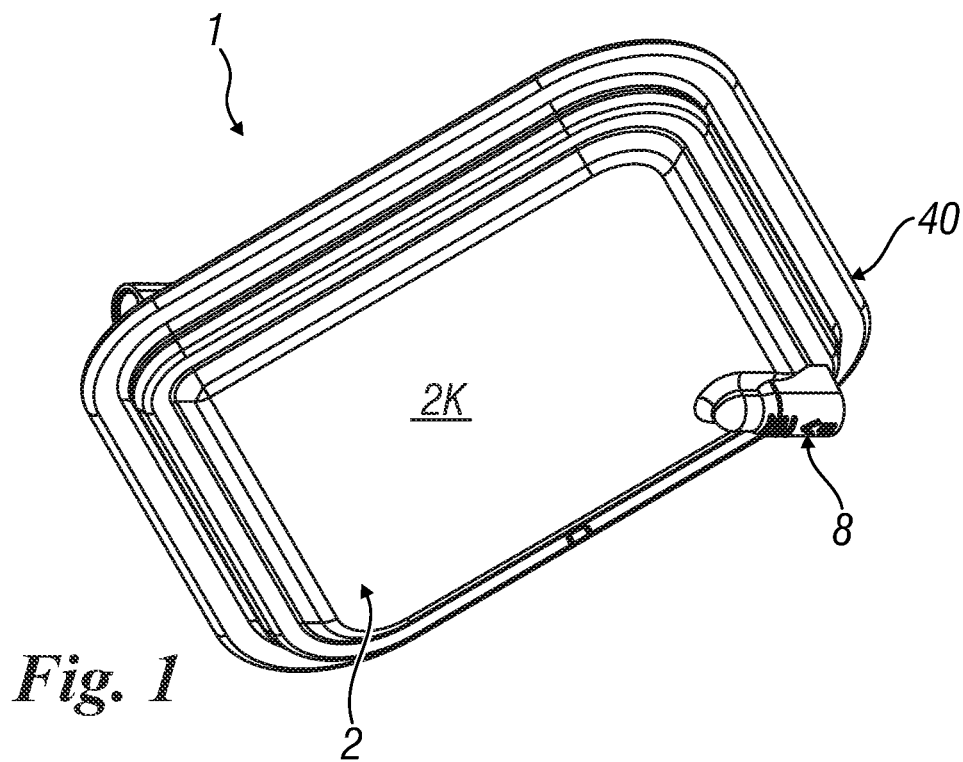
FIG. 1 and FIG. 2 show perspective views from different angles of a filter unit obtained according to the disclosure.
Figure 2:
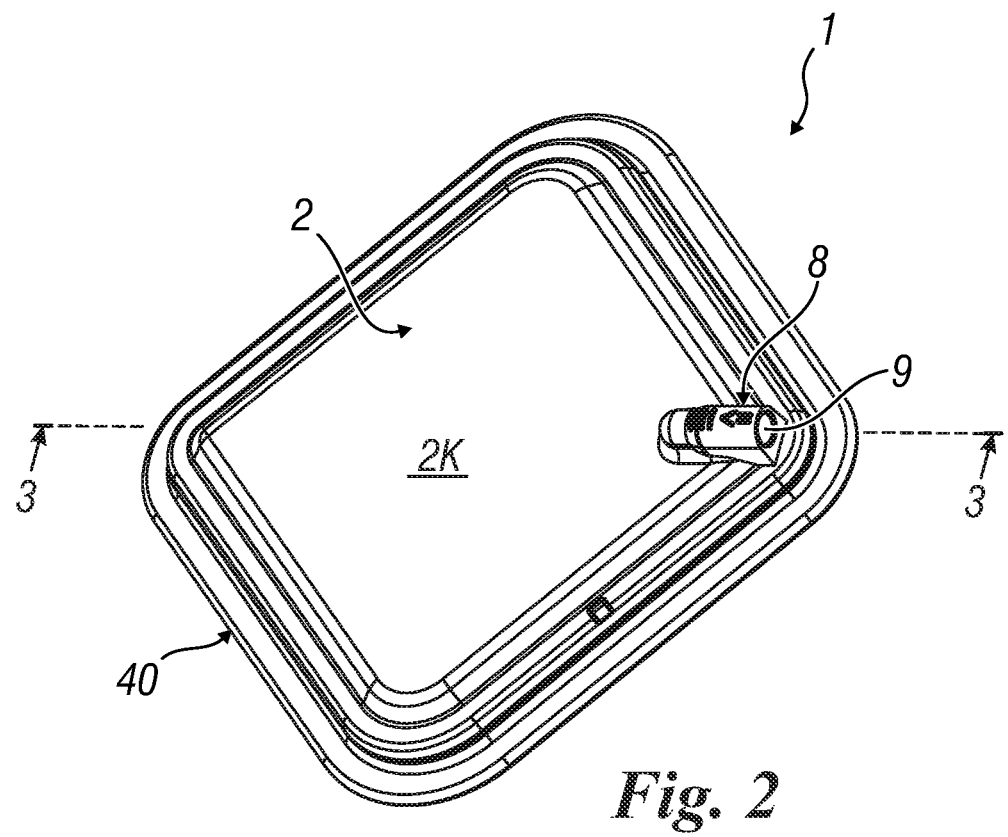
Figure 3:
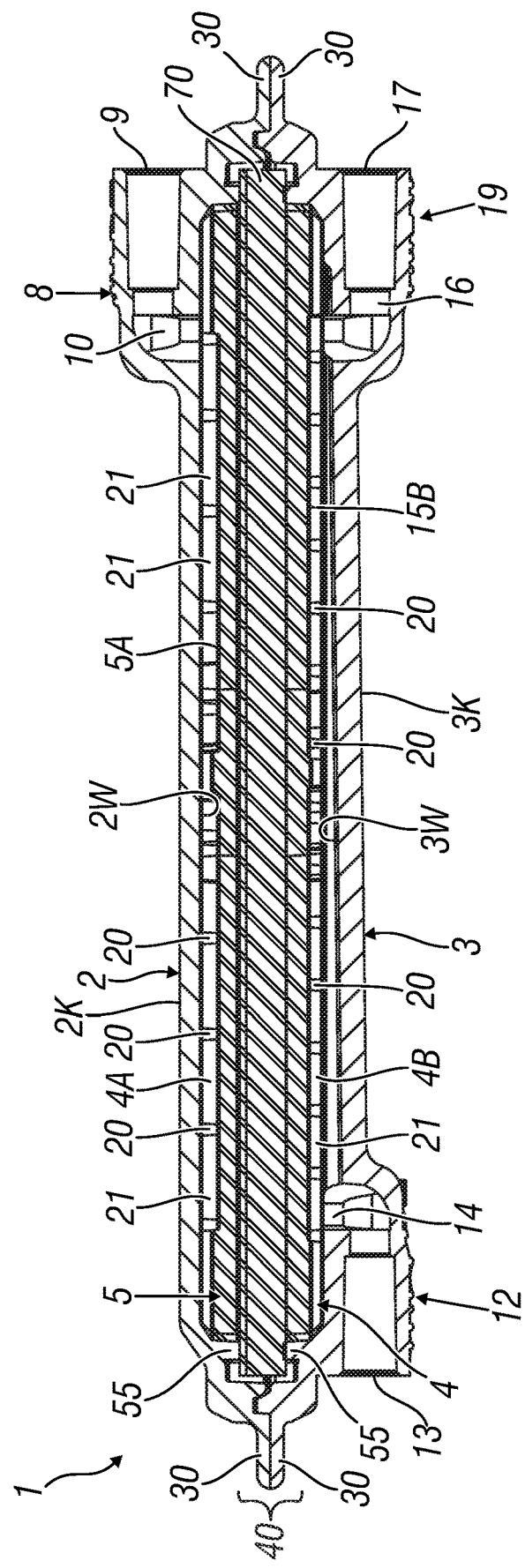
FIG. 3 shows a cross-section view along the line 3-3 in FIG. 2.
Figure 4:
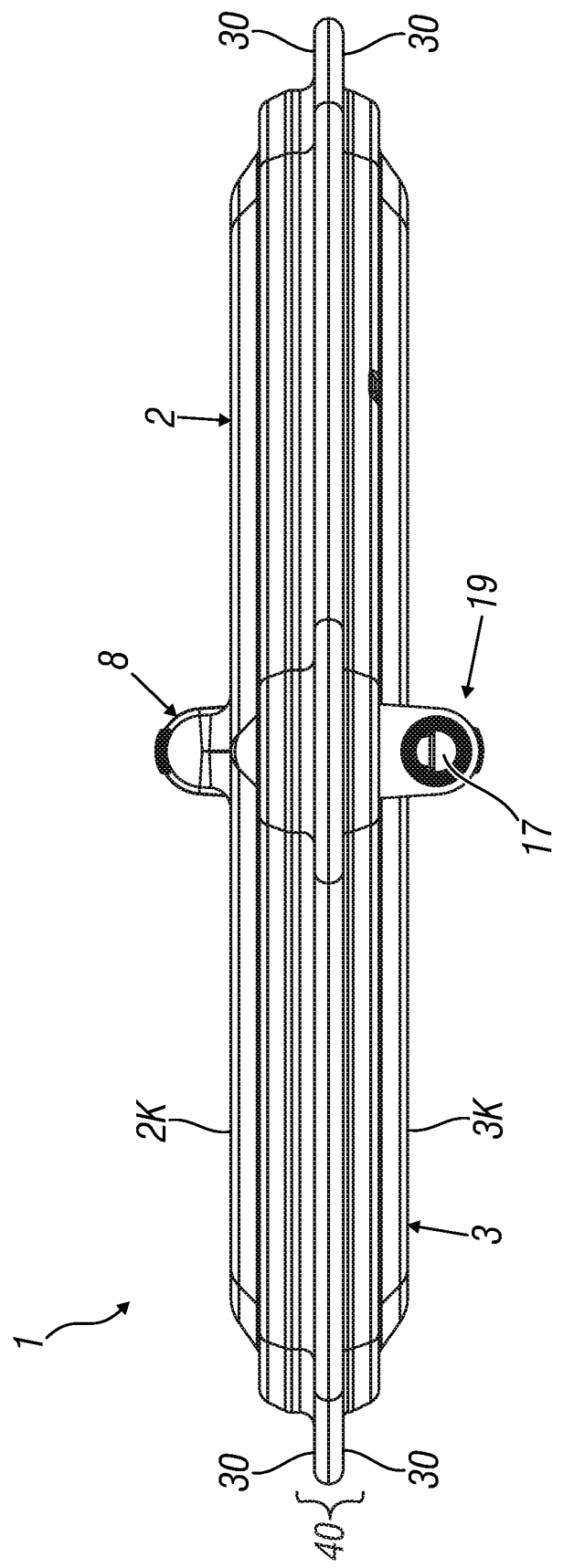
FIG. 4 shows a side view of the filter unit in FIG. 1.
Figure 5:
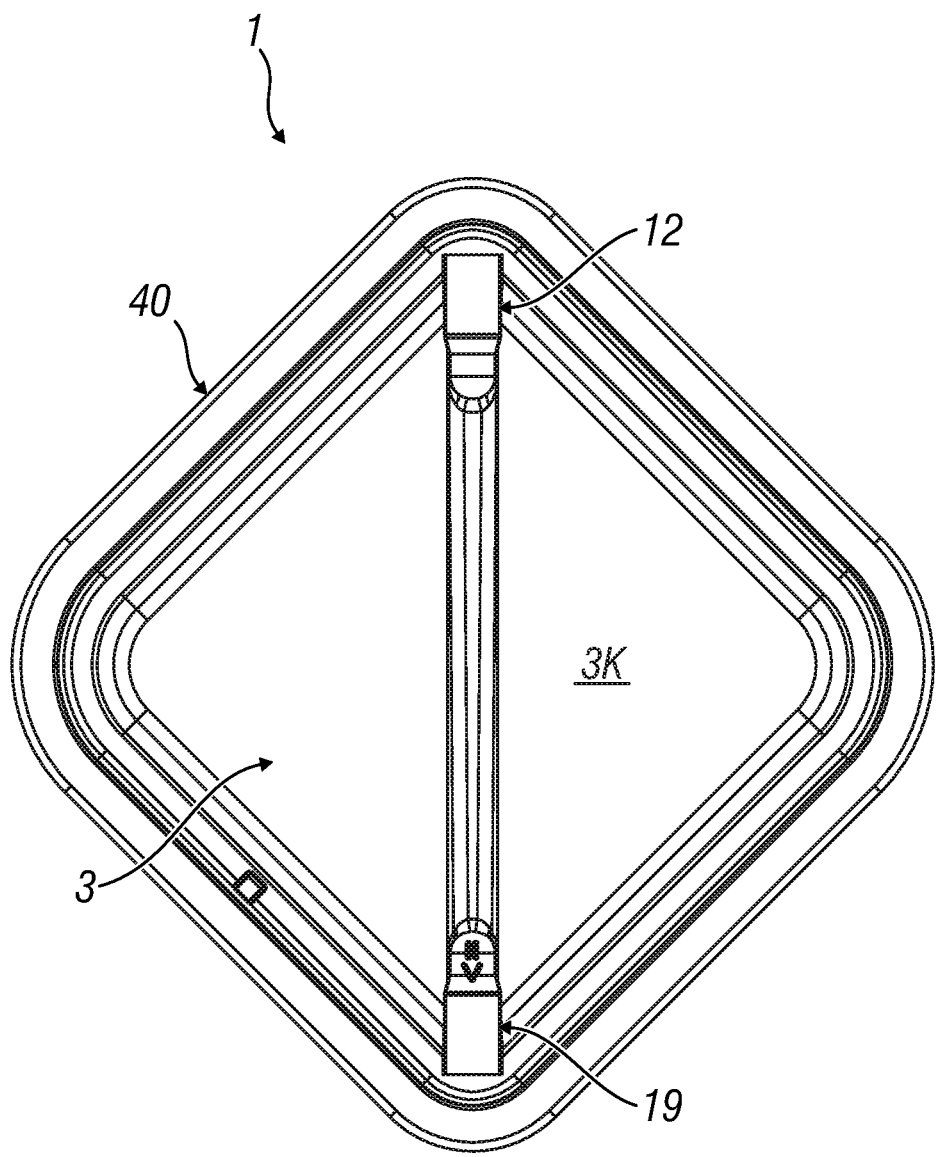
FIG. 5 shows a plan view of the filter unit from the side opposite that shown in FIGS. 1 and 2.
Figure 6:
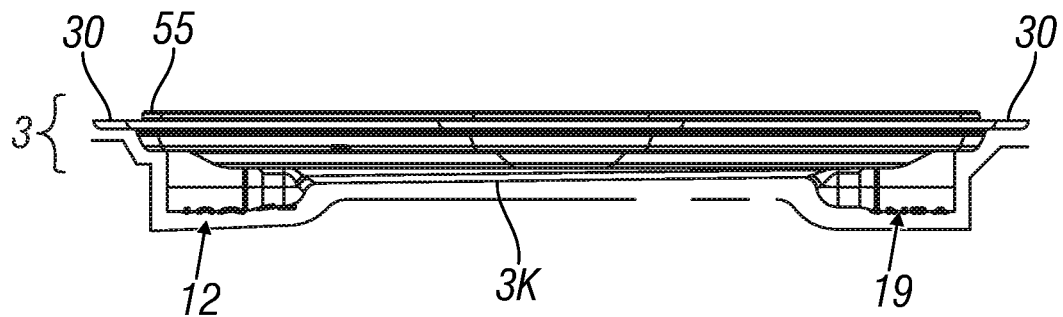
FIG. 6 shows a side view of a component of the filter unit in FIGS. 1 and 2.
Figure 7:
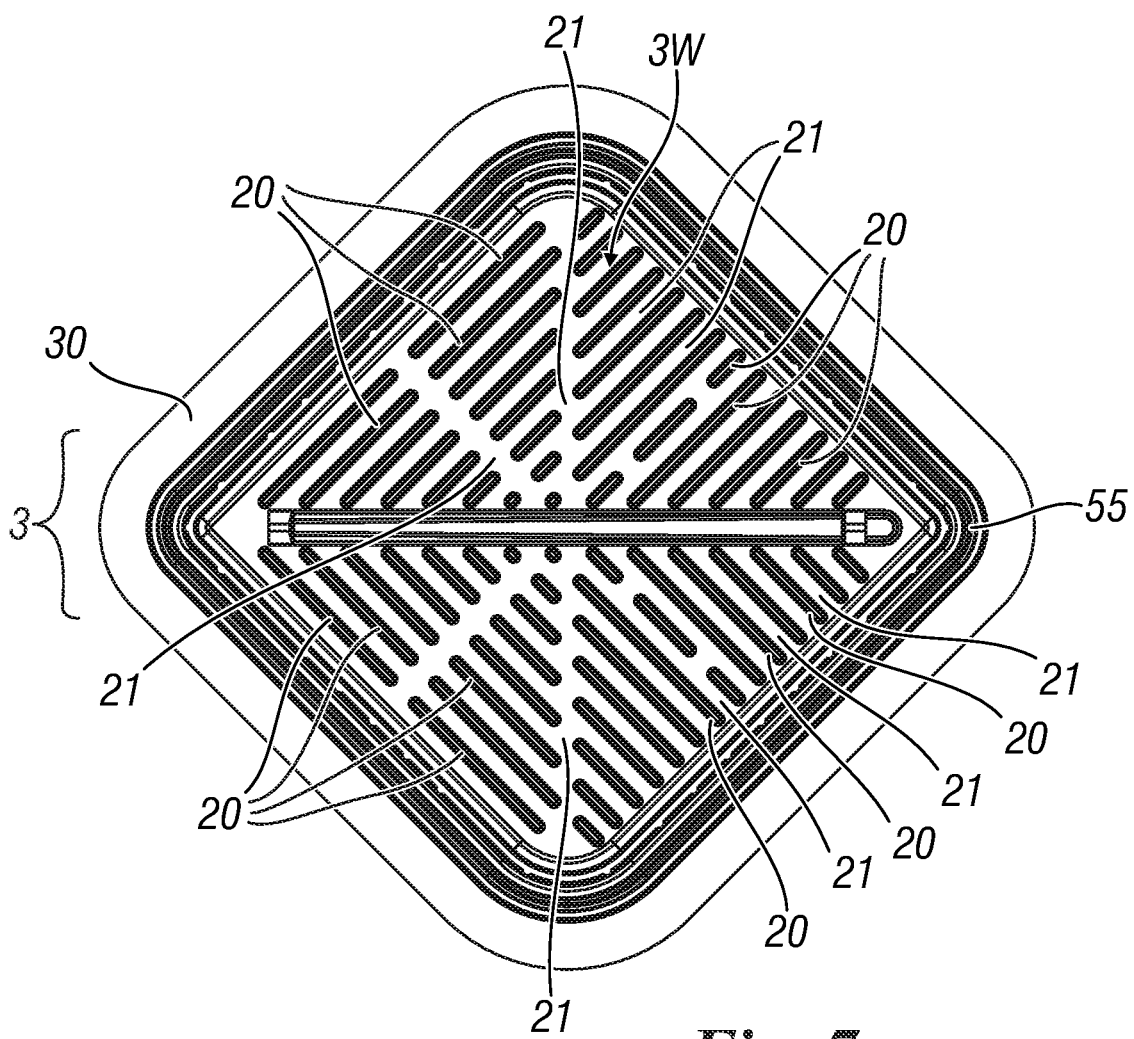
FIG. 7 shows a view from above of the component shown in FIG. 6, the side of this component shown in FIG. 7 being within the filter unit in FIGS. 1 and 2.

First half-shell 2 (positioned on top in FIGS. 2 and 3, for example) has a pierced external appendage 8 and an opening at 9. Between such appendage 8 (of one piece with half-shell 2) there is a conduit 10 which opens into first cavity part 4A.

Similarly, second half-shell 3 (below in FIG. 3) comprises a first pierced external appendage 12, of one piece with half-shell 3, opening at 13 and having a conduit 14 opening into second cavity part 4B. A conduit 16 made between a second pierced external appendage 19 opening at 17 also opens into this cavity part 4B.

Shells 2 and 3 are obtained by injection moulding and have the corresponding appendages of one piece with them. First appendage 8 can be attached to a flexible PVC, polyurethane or the like tube (not shown), second appendage 12 can also be attached to a flexible tube. Third appendage 19 only acts as a vent hole for the air present in filter 1 when second cavity part 4B receives blood or the blood-derivative fluid from first cavity part 4A through the filter element.

Each half-shell 2, 3 has a first side 2K, 3K which defines a corresponding outer face of body 1, and a second face 2W, 3W, opposite the first, bounding cavity 4 (and therefore within body 1). On this second face 2W and 3W each half-shell 2, 3 has a plurality of ribs 20 of different lengths bounding a set of channels 21.

These channels 21 in first half-shell 2 cause the fluid entering first cavity part 4A to become distributed over all a corresponding face 5A of filter element 5 (the face facing such cavity part 4A). In this way the fluid (for example blood) is correctly filtered through such element 5.

Similarly, channels 20 in second half-shell 3 direct such filtered fluid present in second cavity part 4B towards appendage 12, from which it is drawn off.

Filter element 5 and its opposing faces 5A, 5B is also supported on these ribs 20; the ribs ensure overall planarity and rigidity for such filter element 5, which is essential to obtain a correct distribution of blood fluid, in addition to having a correct containment factor for the filter element which is necessary to ensure that it has optimum filtering efficiency, as will be further indicated below.

Half-shells 2, 3 are made of semi-rigid thermoplastic polymer material having a Shore A hardness of between 85 and 95. A material having these characteristics will also be indicated in this document as imparting a semi-rigid yielding property to body 1. In other words, body 1 will also be indicated as being "semi-rigid and yielding", with the characteristics which will be indicated below.

Suitable materials are known and are for example PVC, SBS, PU or the like.

These half-shells 2, 3 are injection moulded. Thanks to the hardness of the material from which they are obtained, half-shells 2, 3 have a soft damping action in relation to impacts against external components. This is particularly advantageous during washing in a centrifuge because it prevents the components of the blood sampling and processing system (bags, tubes, filter units) present in such centrifuge from being broken in the event of contact with body 1.

In addition to this, the (intrinsic) rigidity of the material used to make the half-shells makes it possible to adjust the density of filter element 5 (which, as mentioned, is usually defined by a plurality of filtering layers). It is in fact known that the efficiency of such element 5 is linked to its compression factor or "packing factor". This is provided by the ratio between the density of the (layer-shaped) compressed filtering element and the density of the same filtering element when not compressed.

Using a filter unit 1 having a filtering element 5 with different packing factors changes in the filtering efficiency of unit 1 have in fact been found, as may be seen from the table below.

| PACKING FACTOR % | LEUCOCYTE/ UNIT POST | WBC LOG REDUCTION |
| --- | --- | --- |
| =100% | 4.97E+04 | 4 |
| =110% | 4.37E+04 | 5 |
| =140% | 3.88E+04 | 6.3 | where
Packing Factor=compression factor as indicated above
Leucocyte/Unit Post=[residual leucocytes]
WBC Log Reduction=[logarithmic reduction]

It will be seen from the above how filtration efficiency is linked to the compression factor of the filtering element: the higher that factor, the greater the filtering capacity. This means that, for the same filtering elements, the filter unit in which such elements are not very compressed will filter less well than a filter unit in which such elements are more compressed.

Through the particular choice of the hardness of the materials making up shells 2 and 3 of body 1, the disclosure makes it possible to obtain a sufficiently rigid filter unit to be able to contain a filter element which has undergone light compression and is at the same time sufficiently rigid to be able to suitably protect such element and make it easy to handle. At the same time, this hardness makes it possible to obtain a filter unit which is sufficiently soft not to damage other filter units, tubes, bags or other components of a blood sampling and processing system when this, together with similar systems, is placed in a centrifuge to perform the normal operations to which such systems are subjected.

Three filter units according to "configurations", 1, 2 and 3 in the table shown above were made in order to test the filtration efficiency of a filter unit according to the disclosure.

In particular, in a first configuration (configuration 1) the filter unit comprised a filtering element 5 formed by a pack of forty filtering layers of PET/PBT having a theoretical thickness for each layer of 0.31 mm and a weight per surface area of 52 g/m2. In a second configuration ("configuration 2") only the number of layers in the filtering element (now thirty six) was varied, and in a third configuration ("configuration 3") the number of layers in the filtering element was again changed, to fifty.

A set of three filter units for each configuration of the filtering means was prepared. A filter unit with PVC half-shells, but with different rigidities, that is a first unit having semi-rigid half-shells according to the disclosure (Shore A rigidity 93±2), with soft half-shells (Shore A rigidity 85±2) and with rigid half-shells (H358/30 rigidity 95 MPa) was produced for each configuration.

Given that filter units having rigid half-shells make it possible to have a high packing factor (in that it is possible to create a high pressure on the inner filtering element), when reading the table shown above it is important to compare it with the example for a filtering unit obtained using rigid material.

The various configurations of filter units (with a filtering element obtained in different ways) were used in a filtration test according to a test protocol comprising the following characteristics:

| | |
|---|---|
| Number of leucocytes/unit* | 2.5-3.0 *109 |
| Number of platelets/unit* | depends on the method of centrifuging |
| Temperature of the blood to be filtered | between 4° C. and ambient temperature |
| Age of the blood unit to be filtered | max 10 days after donation |
| Haematocrit (Hct)/unit* | 0.65-0.75 added solution 0.50-0.70 |
| Minimum haemoglobin content/unit* | 45 g |
| Unit volume* | 280+ ml |
| Distance between the unit of blood to be filtered and the collection bag | 180 cm |
| Leucocyte counting method | Nageotte chamber, DNA marking or cytofluorometry |
| Priming of the filter | YES |

The results shown in the table below were obtained using the various units according to the different configurations.

| | Semirigido | | | | Morbido | | | | Rigido | | |
|---|---|---|---|---|---|---|---|---|---|---|---|
| | H Semirigido | Desnitá nel filtro [gr/dm3] | Packing factor | Efficienza Semirigido | H Morbido | Desnitá morbido [gr/dm3] | Packing factor | Efficienza morbido | H Rigido | Desnitá rigido [gr/dm3] | Packing factor | Efficienza morbido |
| Configurazione 1 | 10 | 208 | 124% | 5 LOG | 12 | 173 | 103% | 3.5 lOG | 10 | 208 | 124% | 5 LOG |
| Configurazione 2 | 10 | 187 | 112% | 4 LOG | 10 | 187 | 112% | 4 LOG | 10 | 187 | 112% | 4 LOG |
| Configurazione 3 | 11.5 | 226 | 135% | 6 LOG | 14 | 186 | 111% | 4 LOG | 10 | 260 | 115% | 6.5 LOG |

When what is shown in the above table is examined it will be noted that the filter units with semi-rigid body 1 have a density in the filter which is comparable to filter units with a rigid body with a consequent equivalent or identical packing factor. Vice versa, in the case of filter units with a soft body, the density in the filter is lower and the packing factor is also lower.

The tests performed therefore demonstrate how the disclosure has the advantages associated with the fact that body 1 of the filter unit is of the yielding and semi-rigid half-shells indicated above, but at the same time has a packing factor of more than 110% and is in any event comparable with the packing factor of known rigid filter units.

Each half-shell 2, 3 has a perimetral flange 30 projecting laterally from the shell. Flanges 30 of the two half-shells 2, 3 overlap when body 1 is formed and form an assembly (a perimetral flange 40 projecting from body 1) which is flexible (thanks to the material of which the half-shells are made) so that it can be comfortably handled.

In addition to this, body 1 obtained in this way remains intact during the centrifuging process thanks to the flexibility and anti-impact properties of the semi-rigid or soft material, at the same time making it possible not to damage components of the adjacent blood sampling and processing systems (as indicated above) while centrifuging is in progress.

Flanges 30 are welded together over their entire surface area along a single weld line and without any foreign component placed between them, and in particular without any filter element being present between them. The weld is normally made by heat welding or through the use of ultrasound and, thanks to the fact that it is made directly between uniform parts of the same material, the weld is durable and remains strong over time. The weld line is preferably continuous.

Flanges 30 are made in such a way that when welded the thickness resulting from fusion is between 1 and 2.5 mm, and this, in combination with the material having a hardness in the preselected range indicated above helps to obtain a soft flange 40 which is comfortable to use.

Such flange 40 may also be of variable thickness, diminishing outwards.

Filtering element 5 is held by half-shells 2 and 3, in addition to ribs 20, and also through projecting ledges 55 located close to the edges of those half-shells on faces 2W and 3W of said half-shells, close to their perimetral edge. These shelves 55, which may be continuous on each face 2W or 3W or discontinuous, form a kind of (continuous or discontinuous) ring which presses on faces 5A and 5B of filtering element 5 securing that element between the half-shells. In particular, these shelves 55 press said filtering element 5 close to its perimetral edge 70 of small thickness.

Thanks to this the modular combination of the number and type of filtering layers can be varied without interfering with the welding of flanges 30 and the consequent closing off of the perimeter of body 1 in that the filtering module does not interfere with the welding of the half-shells, but is wholly contained within them and compressed at its perimetral edge thus obtaining a product (the filtration unit) having performance characteristics suitable for specific applications or different types of blood derivatives.

As mentioned, shelves 55 close off the periphery of cavity parts 4A and 4B. This feature, together with the configuration of ribs 20 bounding and defining channels 21, allows the fluid entering the filtering unit via appendage 8 to be conveyed in an optimum way towards filtering element 5 and, after passing through the latter, towards appendage 12. This avoids bypassing filtering element 5 at its perimetral edge 70.

Through the disclosure a filter unit having the characteristics described above is obtained. Other embodiments are however possible while remaining within the scope of the disclosure defined by the following claims.

The invention claimed is:

1. Filter unit for blood and blood derivatives comprising a body defined by two injection-moulded half-shells of thermoplastic polymer material, there being present between said half-shells a cavity containing a filtering element having two opposing flat faces, an inlet opening and an outlet opening made on the opposing outside surfaces of said body communicating with said cavity, wherein each of said half-shells comprises a projecting perimetral flange, the perimetral flanges of the overlapping half-shells in direct contact and welded together along a single weld line to define a flange of the body of the filter unit and join the two half-shells together, each perimetral flange projecting outwardly away from the cavity to define an inner surface, a first inner surface of a first half shell being mated to and directly engaged with a second inner surface of a second half shell, the filtering element being wholly contained within cavity of the body and pressed by shelves projecting into the cavity from each half-shell, at least in the vicinity of one of the perimetral edges and on the two opposing faces, said shelves holding said filtering element in a stable position within cavity, said thermoplastic polymer material being yielding and semi-rigid, the thermoplastic polymer material having a Shore A hardness of between 85 and 95.

2. Filter unit according to claim 1, wherein the filter has a packing factor of more than 100%.

3. Filter unit according to claim 1, wherein the perimetral flange of the two half-shells and therefore the flange of body of the filter unit projects by between 2 and 5 mm along the edges of the body.

4. Filter unit according to claim 3, wherein said perimetral flange of the body of the filter unit has a thickness which decreases outwards moving away from said body.

5. Filter unit according to claim 1, wherein said shelves are one of continuous or discontinuous and define a continuous or discontinuous ring close to the edges of the half-shells.

6. Filter unit according to claim 1, wherein the edge of the filtering element has a smaller thickness relative to the remaining part of said filtering element.

7. Filter unit according to claim 1, wherein said half-shells have a face facing the cavity of said body of the filter unit, and wherein ribs project from the face and are configured for pressing against the opposing faces of the filtering element, said ribs defining channels between them configured to encourage the movement of blood and blood derivative from inlet opening to outlet opening of said body of the filter unit.

8. Filter unit according to claim 1, wherein said inlet opening and said outlet opening are provided within appendages projecting from faces of said half-shells forming outer faces of body of the filter unit, said appendages being of one piece with the said half-shells.

9. Filter unit according to claim 8, further comprising a third appendage projecting from a face of one of said half-shells, said third appendages defining a vent hole being of one piece with the said half-shells.

10. Filter unit according to claim 1, wherein the perimetral flanges do not press against the filtering element.

* * * * *